United States Patent [19]
Keay et al.

[11] Patent Number: 5,962,645
[45] Date of Patent: Oct. 5, 1999

[54] ANTIPROLIFERATIVE FACTOR FROM PATIENTS WITH INTERSTITIAL CYSTITIS

[75] Inventors: Susan Keay, Ellicott City; John W. Warren; Michael Kleinberg, both of Baltimore; Michael K. Hise, Ellicott City, all of Md.

[73] Assignee: University of Maryland, Baltimore, Md.

[21] Appl. No.: 08/944,202

[22] Filed: Oct. 3, 1997

Related U.S. Application Data

[60] Provisional application No. 60/027,646, Oct. 4, 1996.
[51] Int. Cl.$^6$ .............................. C07K 1/00; C12G 1/00; G01N 33/574
[52] U.S. Cl. .............................. 530/350; 435/4; 435/7.23
[58] Field of Search ...................... 435/4, 7.23; 530/350

[56] References Cited

PUBLICATIONS

Tao et al., J Immunology, 143: 2595–2601, 1989.
Lazar et al. Molecular and Cellular Biology 8: 1247–1252, 1988.
Burgess et al., J Cell Biol. 111: 2129–2138, 1990.

*Primary Examiner*—Paula K. Hutzell
*Assistant Examiner*—Lin Sun-Hoffman
*Attorney, Agent, or Firm*—Chalin A. Smith, Office of Research & Development

[57] ABSTRACT

A novel antiproliferative factor (APF) present in urine of patients with interstitial cystitis (IC) is described. This urine antiproliferative factor can serve as a marker for disease activity and its antagonists as therapeutic medicaments for IC. In addition, APF and its agonists can be used for treating diseases associated with cell proliferation.

4 Claims, 13 Drawing Sheets

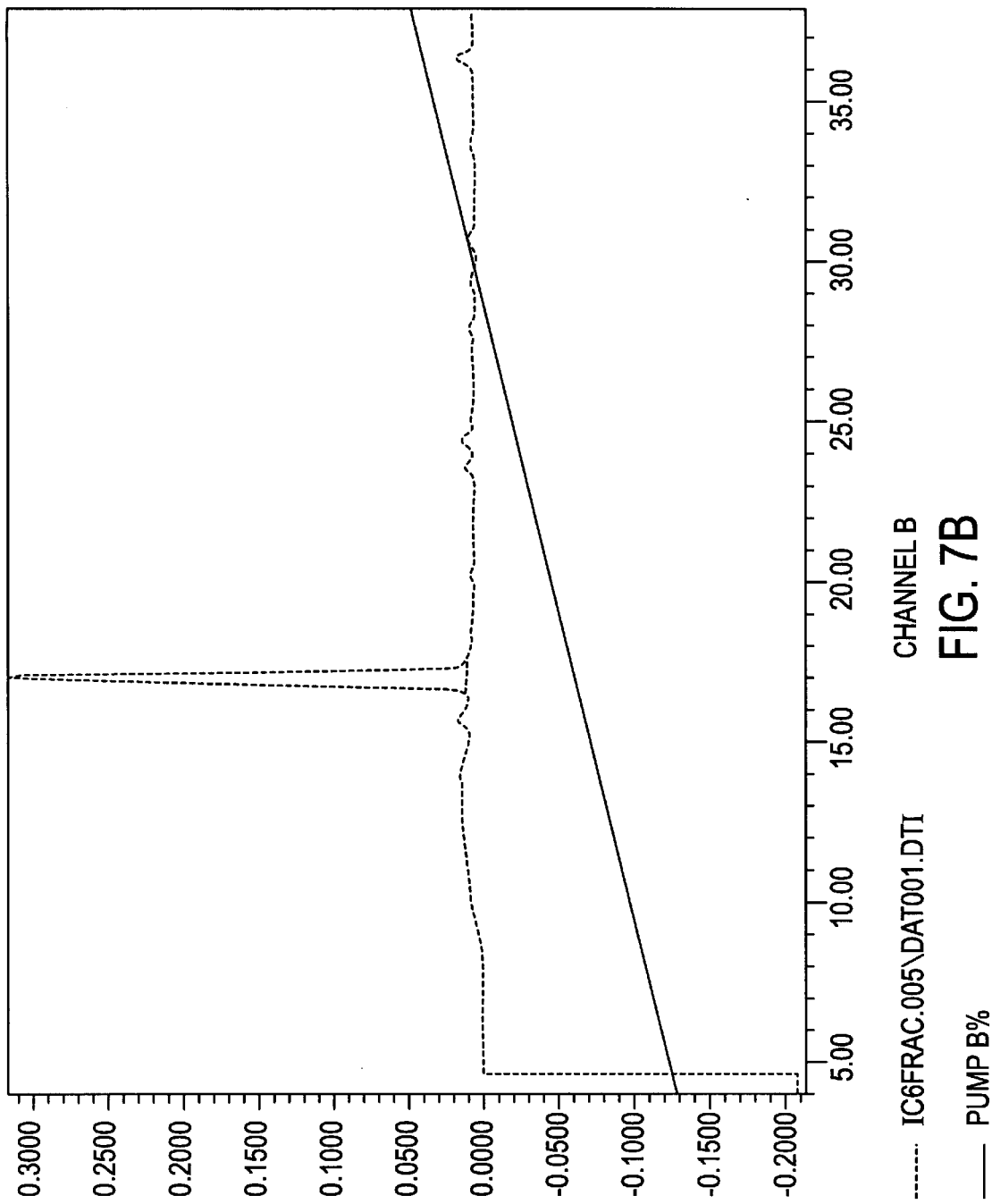

|  | PMOLES | MOLE% | RESIDUES/MOLE |
|---|---|---|---|
| CYS ACID | 0.00 | 0.00 | 0.00 |
| ASX | 70.59 | 5.693 | 1.573 |
| THR | 68.03 | 5.487 | 1.516 |
| SER | 52.74 | 4.253 | 1.175 |
| GLX | 145.17 | 11.708 | 3.235 |
| PRO | 57.69 | 4.653 | 1.286 |
| GLY | 489.24 | 39.458 | 10.903 |
| ALA | 63.22 | 5.099 | 1.409 |
| VAL | 59.53 | 4.801 | 1.327 |
| MET | 10.26 | 0.829 | 0.229 |
| ILE | 40.31 | 3.251 | 0.898 |
| LEU | 79.16 | 6.384 | 1.764 |
| TYR | 16.97 | 1.369 | 0.378 |
| PHE | 26.52 | 2.139 | 0.591 |
| HIS | 7.94 | 0.641 | 0.177 |
| LYS | 33.01 | 2.662 | 0.736 |
| TRP | 0.00 | 0.00 | 0.00 |
| ARG | 19.55 | 1.575 | 0.435 |

FIG. 9

ANTIPROLIFERATIVE FACTOR FROM PATIENTS WITH INTERSTITIAL CYSTITIS

This application claims the benefit of U.S. Provisional Application Ser. No. 60/027,646, filed on Oct. 4, 1996.

The development of the present invention was supported by the University of Maryland, Baltimore, Md. and by funding from the National Institutes of Health under grant number DK 44818. The United States Government has a non-exclusive, irrevocable, paid-up license to practice or have practiced for or on behalf of the United States the invention herein as provided for by the terms of the above mentioned contracts awarded by the United States Government.

BACKGROUND OF THE INVENTION

Interstitial cystitis (IC) is a chronic bladder disorder which affects up to 450,000 women in the United States; approximately one-tenth as many men also suffer from this condition [Ratner, et al. (1994) *Urol. Clin. North Am.* 21:1–5; Hanno et al. (1990) *Interstitial Cystitis*, London: Springer-Verlag]. Interstitial cystitis often has a rapid onset with pain, urgency and frequency of urination and cystoscopic abnormalities including petechial hemorrhages (glomerulations) or ulcers that extend into the lamina propria (Hunner's ulcers) [Oravisto, K. J. (1975) *Ann. Chir. Gynaecol. Fenn.* 64: 75]. Certain features of the bladder epithelium suggest that the epithelial barrier is abnormal in IC. For example, the bladder mucin layer is sometimes damaged [Johansson and Fall (1990) *J. Urol.* 143:1118; Smith and Dehner (1972) Arch. Pathol. 93:76], the bladder epithelium can be denuded resulting in ulceration [Oravisto, ibid; Smith, ibid] and intraurothelial Tamm-Horsfall protein is sometimes found [Fowler et al. (1988) *J. Urol.* 140:1385]. The rapid onset of IC is followed by a chronic course with partial remissions and reexacerbations, which can continue for up to 30 years [Hanno, ibid.] No etiology for IC has yet been identified, and no empiric treatment has been proven to be reliably efficacious.

The diagnosis of IC currently requires cystoscopy and bladder biopsy, with either of two distinct mucosal abnormalities (Hunner's ulcers or glomerulations) being diagnostic of this disorder.

Therefore, there is a need for a faster, less invasive method for diagnosing IC in patients.

SUMMARY OF THE INVENTION

The antiproliferative factor and method of using described in the present invention fulfills the above need.

In this invention is described a novel antiproliferative factor found in urine of IC patients which inhibits proliferation of primary normal adult human bladder epithelial cells in vitro.

The discovery of this novel antiproliferative factor (APF) was based on the following: both of the diagnostic lesions seen in IC are characterized by epithelial abnormalities. Although an inflammatory cell infiltrate is common in the 10% of IC patients with Hunner's ulcers, it is less prominent in the 90% of IC patients with glomerulations in whom the predominant histologic feature is epithelial tears with submucosal hemorrhage. Therefore, this would indicate that epithelial abnormalities are the cardinal feature of this syndrome. In addition, urinary diversion procedures have resulted in improvement or resolution of bladder symptoms in some cases [Freiha et al. (1980) *J. Urol.* 123:632–634], suggesting that the bladder epithelial damage may result from exposure to urinary solutes.

Therefore, we looked at whether urine from IC patients can induce specific morphologic or physiologic abnormalities in primary normal adult human bladder epithelial cells. We discovered that the urine of IC patients inhibits the proliferation of normal bladder epithelial cells in vitro, and that this antiproliferative activity is due to a low molecular weight, heat stable peptide which can be used as an indicator for this disease.

Therefore, it is one object of the invention to provide an antiproliferative factor (APF) substantially free of natural contaminants, or derivatives thereof.

It is another object of the present invention to provide an antiproliferative factor with a molecular weight of about 1671 Da, which is heat stable having a pI of about 1.38–3.5, which inhibits the proliferation of several different cell types in vitro, including normal bladder epithelial (HBE) cells and bladder carcinoma cells, as determined by inhibition of $^3$H-thymidine or bromodeoxyuridine incorporation.

It is another object of the present invention to provide a method for diagnosing interstitial cystitis in a patient which comprises assaying for the presence of APF.

It is yet another object of the present invention to provide a method for treating a disease associated with APF which comprises providing to an individual in need of such treatment an effective amount of an agent which inhibits APF.

It is a further object of the present invention to provide a therapeutic medicament comprising anti-APF or an agent which inhibits APF.

It is yet a further object of the present invention to provide a therapeutic medicament comprising APF or an agonist of APF for treating a disease associated with an increase in cell proliferation such as tumourigenesis or cancer.

BRIEF DESCRIPTION OF THE DRAWINGS

FIG. 7B: Determination of APF purity by HPLC.

FIG. 9: Amino acid analysis of APF.

DETAILED DESCRIPTION OF THE INVENTION

Indirect evidence for a urinary cytotoxin in IC was first reported by Clemmensen and colleagues in 1988 who demonstrated a toxic or allergic reaction in skin patch tests to a substance present in greater amounts in IC patients' urine to which IC patients were more sensitive [Clemmensen et al. (1988) *Urology* 32: 17]. Subsequent attempts to identify a urinary cytotoxin in IC indicated the presence of a toxin with molecular mass <3,500 daltons [Parsons and Stein (1990) *J. Urol.* 143: 373A], however, other studies using a rabbit model infused with IC or control patient urine specimens suggested the presence of a urinary toxin with molecular mass>10,000 d. [Ruggieri et al. (1993) *Urology* 42:646]. The most recent report, which used a chromium-51 release assay in transitional epithelial cells or erythroleukemia cells, found no toxic effect from IC patient urine [Beier-Holgersen et al. (1994) *J. Urol.* 151: 206].

We used a sensitive cell proliferation assay in which $^3$H-thymidine incorporation is measured in either nonmalignant or malignant human bladder cells. With this assay, significant differences from urine from control patients were noted for urine from IC patients within 48 hours indicating the presence of an antiproliferative substance. The approximate molecular weight of the antiproliferative urinary substance was subsequently established by dialysis and ultrafiltration, to be about 1–3 kD. Further characterization by heat treatment and trypsination indicated that the APF is heat stable, trypsin-sensitive factor.

Purifying APF

Purification of the antiproliferative factor (APF) was performed by preparing <10 kDa fractions from urine specimens of IC patients using filters for fractionation of specimen by size such as "CENTRIPREP" filters (Amicon, Beverly, Mass.). APF was then further purified from these fractions by protein purification methods known to people in the art which separate protein based on charge, hydrophobicity, and size, including ion-exchange and hydrophobic interaction chromatography and high performance liquid chromatography (HPLC).

Briefly, APF was purified as follows. Each purified fraction was desalted by dialysis and the ability of a fraction to inhibit $^3$H-thymidine incorporation in human bladder epithelial (HBE) cells assessed as described below by performing the HBE cell proliferation assay; results obtained from IC patient urine fractions were compared to results obtained using urine from age-, race-, and sex-matched controls.

Figure 4:
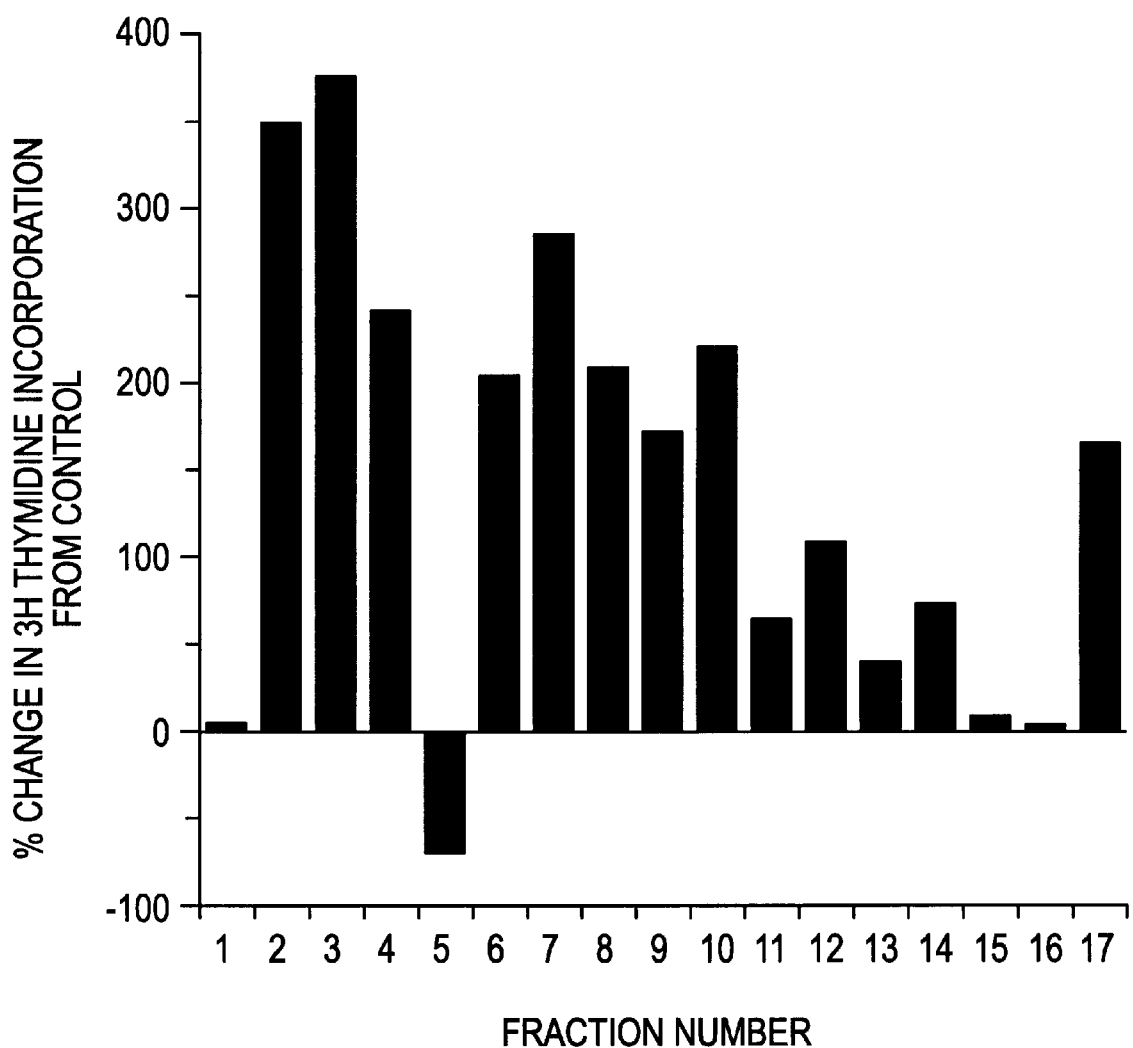
FIG. 4: Separation of urinary components by HPLC.

Reversed-phase high performance liquid chromatography (HPLC) was first demonstrated to be useful for further purification of the antiproliferative peptide (FIG. 4). The <10 kDa urine fractions from 2 IC patients and 2 controls were dialyzed against 10 mM sodium phosphate buffer, after which the dialysates were lyophilized, dissolved in water (50 fold concentration), and passed through 0.2 mm filters to remove particles. A 50 ml sample of each specimen was injected onto a C18 column (octadecyl aliphatic groups bonded to silica, Vydak, Hesperia, Calif.) and eluted with a 0–20% acetonitrile gradient [using 0.1% trifluoroacetic acid (TFA) in water (buffer A) and acetonitrile in 0.08% TFA (buffer B)]. Samples were dialyzed against phosphate buffered saline to remove acetonitrile and TFA, diluted 1:2 in serum-free cell culture medium, and incubated with HBE cells (48 hours at 37° C.). Analysis of subsequent $^3$H-thymidine incorporation indicated the presence of a single fraction containing antiproliferative activity in each IC specimen (data shown for one patient, FIG. 4) which included 2 protein peaks by optical density tracing at 215 nm. No inhibitory fraction was identified in the <10 kDa fraction from the age-, race- and sex-matched controls.

Figure 6:
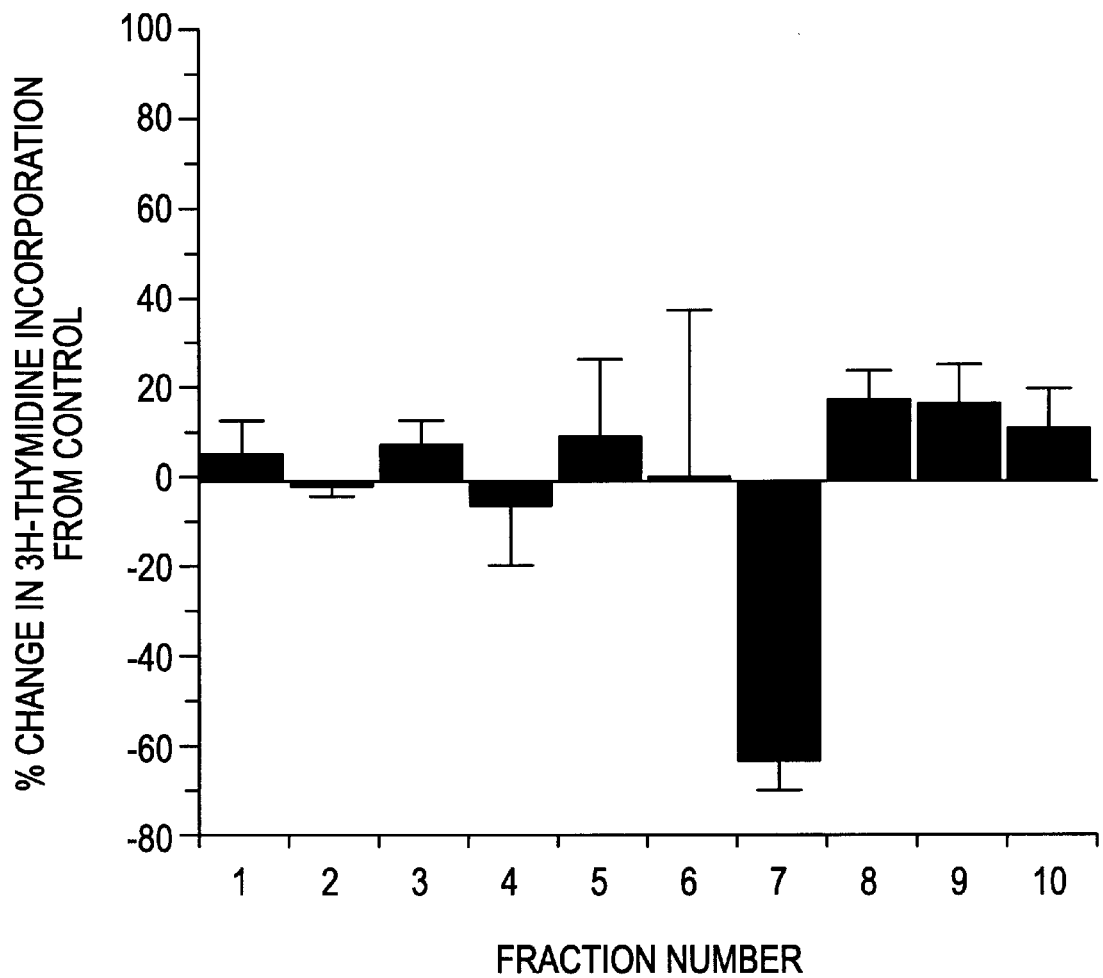
FIG. 6: Separation of low molecular weight urinary components by hydrophobic interaction chromatography.

Hydrophobic interaction chromatography using a variety of matrices revealed the ability of a phenyl sepharose 6 fast flow (high sub) matrix (Pharmacia Biotech, Uppsala, Sweden) to be useful for analytical APF purification. The <10 kDa fraction from 10 ml of IC or control urine was adjusted to pH 6.0 with 10 N NaOH then diluted to 300 mOsm with double distilled H$_2$O. These preparations were then applied to phenyl sepharose 6 fast flow columns [which were suspended in 1M ammonium sulfate (pH 7.0)] at 4° C.]. Protein was then eluted using 50 mM sodium phosphate buffer (pH 7.0). Run-through and eluted fractions were then dialyzed against phosphate buffered saline (pH 7.0) at 4° C. overnight, diluted 1:3 in serum-free culture medium, and applied to normal human bladder cells for the $^3$H thymidine incorporation assay. By this method a single fraction with antiproliferative activity was able to be obtained from IC urine that was not present in control urine (FIG. 6).

As a preliminary step for choosing an appropriate matrix and buffer system for ion exchange chromatography, the pI of the purified or partially purified APF was determined by isoelectric focusing, using a density gradient electrofocusing apparatus. The pI of APF was found to be in the range of 1.38–3.5. The pH curve was constructed from each sample, and the pH of each sample neutralized prior to performing the HBE cell proliferation assay; isoelectric focusing of the corresponding fraction from normal urine was also done and fractions were collected to serve as negative controls.

Figure 5:
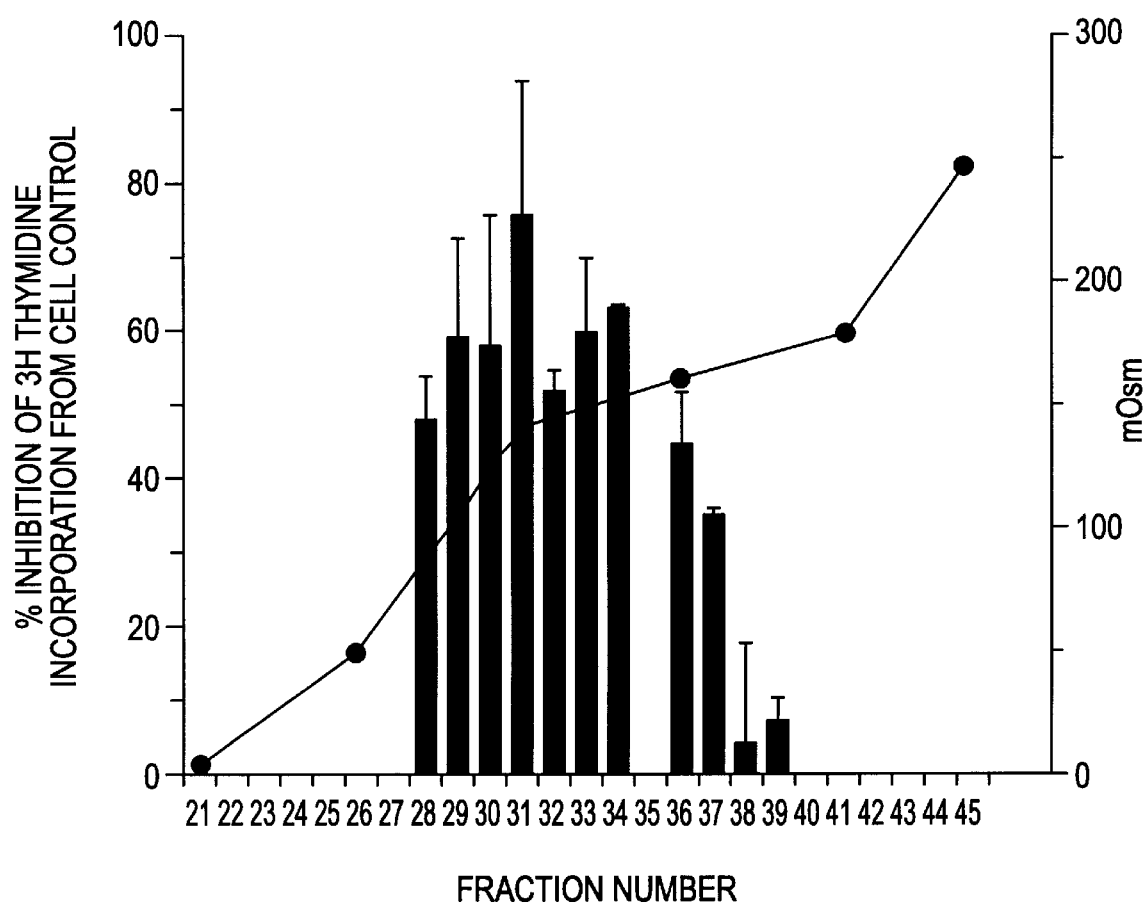
FIG. 5: Separation of urinary components by ion exchange chromatography.

Anion exchange chromatography using a "MONO Q" sepharose column (functional group CH$_2$N.(CH$_3$)$_3$, Sigma, St. Louis, Mo.) also proved to be useful for partial preparative APF purification. The "MONO Q" matrix was suspended in 500 mM phosphate buffer (pH 7.0) and washed with 20 mM phosphate buffer (pH 7.0). The <10 kDa fractions of urine from large IC or control urine collections (500 ml each) were diluted 1:1 in 20 mM phosphate buffer and loaded onto the column at 4° C. overnight. Following a column wash with 20 mM phosphate buffer, protein was eluted with 1 M NaCl in 20 mM phosphate buffer (pH 7.0); fractions were diluted 1:40 in serum-free culture medium and applied to normal human bladder cells for the $^3$H-thymidine incorporation assay. By this method a wide peak of protein with antiproliferative activity was able to be eluted from the IC specimen which was not present in the control specimen (FIG. 5).

A sequential purification scheme which employs each of these three methods (preparative ion exchange chromatography followed by hydrophobic interaction chromatography followed by HPLC) was used to obtain highly purified APF from the low molecular weight (<10 kDa) fraction of urine from IC patients. The purity of the APF was confirmed by optical density tracing of protein in HPLC fractions (at 215 and 280 nm) (FIG. 7B). The molecular weight was determined by mass spectrometry to be 1671 daltons (8).

Antiproliferative activity was easily measured from HPLC fractions of a small amount of urine (50 ml). HPLC experiments rendered a single peak which represented highly pure APF (FIG. 7B) having a molecular weight of 1671 daltons.

Antiproliferative factor was purified to homogenity from urine specimens of patients with IC. Because of its small size, it is possible that APF is filtered by the kidney, or produced by cells in the upper or lower urinary tract. In these cases, APF can be purified from these sources using the methods described above or other methods known to someone with ordinary skill in the art using the guidance provided by this application.

Amino acid analysis was performed and revealed a glycine rich peptide. N-terminal amino acid sequence analysis of purified APF could not be determined by Edman degradation, presumably because of a blocked N-terminus. However, the sequence of peptides generated by cleavage with cyanogen bromide and/or other cleavage can be performed (Oike, Y. et al. (1982) *J. Biol. Chem.* 257: 9751–9758; Liu, C. et al. (1983) Int. *J. Pept. Protein Res.* 21: 209–215); the N-terminus of the APF can also be deacetylated using an acylamino acid-releasing enzyme according to the manufacturer's instructions (Pierce, Rockford, Ill.), or deglycosylated using published methods [Keay and Baldwin, ibid.]. The amino acid sequence of the peptide can be deduced by analysis of the overlapping cleaved peptide fragments. If sequencing data by these methods is not obtainable, partial sequence of the peptide may be obtained by mass spectrometry, and can be compared to sequences of known peptides recorded in GenBank.

APF and its Functional Derivatives, Agonists and Antagonists

The present invention pertains partially to antiproliferative factor (APF), to fragments of this factor, as well as to functional derivatives, agonists and antagonists, and metabolic breakdown products of this factor. The invention especially concerns agents which are capable of inhibiting APF.

A "functional derivative" of APF is a compound which possesses a biological activity (either functional or structural) that is substantially similar to a biological activity of APF, for example induces antiproliferative activity of bladder cells. The term "functional derivatives" is intended to include the "fragments," "variants," "analogues," or "chemical derivatives" of a molecule. A "fragment" of a molecule such as APF, is meant to refer to any polypeptide subset of the molecule. A "variant" of a molecule such as APF is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analogue" or agent which mimics the function of a molecule such as APF is meant to refer to a molecule subtantially similar in function but not in structure to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

Analogues of APF or agents which mimic the function of APF can be used to diagnose the presence of antibody to APF in tissue or urine or for testing drugs which are suspected of inhibiting APF function. Since APF was shown to inhibit growth of T24 bladder carcinoma cells by $^3$H-thymidine assay, APF or APF analogues can be provided to a subject for treatment of bladder cancer or other tumors associated with the absence of APF.

An "antagonist" of APF is a compound which inhibits the function of APF. Such antagonists can be immunoglobulins (such as, for example, monoclonal or polyclonal antibody, or active fragments of such antibody). The antagonists of the present invention may also include non-immunoglobulin compounds (such as polypeptides, organic compounds, etc.)

Polyclonal antibody capable of binding to APF can be prepared by immunizing a mammal with a preparation of APF or functional derivative of APF. Methods for accomplishing such immunizations are well known in the art. Monoclonal antibodies (or fragments thereof) can also be employed to assay for the presence (or amount) or APF in a particular biological sample. Such antibodies can be produced by immunizing splenocytes with activated APF (by modifying the procedures of Kohler et al. [*Nature* 256:495 (1975); *Eur. J. Immunol.* 6:511 (1976); *Euro J. Immunol.* 6:292 (1976)].

In addition to the above methods, antibodies capable of binding to the receptor for APF may be produced in a two step procedure through the use of anti-idiotypic antibodies. Such a method makes use of the fact that antibodies are themselves antigens, and that, therefore, it is possible to obtain an antibody which binds to a second antibody. In accordance with this method, antibodies capable of binding to APF are used to immunize an animal. The splenocytes of such an animal are then used to produce hybridoma cells, and the hybridoma cells are screened to identify clones which produce antibody whose ability to bind to anti-APF antibodies can be specifically blocked by APF protein. Such antibodies comprise anti-idiotypic antibodies to the anti-APF antibody. Such antibodies can be used to immunize an animal, and thereby induce the formation of antibodies capable of binding to APF. Anti-idiotypic antibodies, or other agents which mimic APF, could be used as an antitumor factor.

In addition to providing additional APF (or a functional derivative of APF) to a subject, the efficacy of APF in a subject can be increased by the administration of an agonist of APF to a subject. The invention additionally pertains to such agonists of APF. An agonist of APF is any compound which is capable of increasing the efficacy of a function of APF. Examples of such agonists include an agent which promotes the synthesis of APF by the subject, etc. Agonists can be used to induce APF in normal cells for testing drugs and treatments and for diagnostic purposes. Additionally, anti-idiotypic antibodies, or analogues of APF, or agents which mimic APF activity, or a combination of any of the above can be provided to a subject in need of such treatment.

APF may be obtained synthetically, through the use of recombinant DNA technology, or by proteolysis. The therapeutic advantages of such agents may be augmented through the combined administration of several agents. The scope of the present invention is further intended to include functional derivatives of APF which lack one, two, or more amino acid residues, or which contain altered amino acid residues, so long as such derivatives exhibit the capacity to influence cell proliferation.

The compounds of the present invention are said to be "substantially free of natural contaminants" if preparations which contain them are substantially free of materials with which these products are normally and naturally found. The APF of the present invention has been separated from other urine components such that one peak is evident at 215 nm following HPLC in the fraction that has antiproliferative activity. The APF has a molecular weight of about 1671 daltons, is heat stable, with a pI of about 1.38–3.5, and inhibits the proliferation of several different cell types in vitro, including normal bladder epithelial cells and bladder carcinoma cells, as determined by inhibition of $^3$H-thymidine or bromodeoxyuridine incorporation.

Methods for preparing APF

The antiproliferative factor of the present invention may be obtained by natural processes (such as, for example, by inducing the production of APF from a human or animal cell); by synthetic methods (such as, for example, by using the Merrifield method for synthesizing polypeptides to synthesize APF, functional derivatives of APF, or agonists or antagonists of APF (either immunoglobulin or non-immunoglobulin)); or by the application of recombinant technology (such as, for example, to produce the APF of the present invention in diverse hosts (i.e., yeast, bacterial, fungi, cultured mammalian cells, to name a few), or from recombinant plasmids or viral vectors). The choice of which method to employ will depend upon factors such as convenience, desired yield, etc. It is not necessary to employ only one of the above-described methods, processes, or technologies to produce APF; the above-described processes, methods, and technologies may be combined in order to obtain APF. It is most preferable to prepare APF by cloning and expressing a gene or cDNA sequence which encodes the APF protein. Such gene cDNA sequence hereinafter termed the "APF gene" or "APF cDNA sequence".

Uses for APF and its Functional Derivatives, Agonists and Antagonists

A. Diagnostic Uses

The compounds of the present invention may be used to diagnose the presence of interstitial cystitis in the bladder, by detecting the presence of APF in the urine, or in extracts such as serum, in sections, etc. of organs. In addition to their diagnostic potential, these compounds may also help to determine the pathogenesis of IC.

The presence of interstitial cystitis can be determined by identifying or quantifying the level of APF present in a particular biological sample. Any of a variety of methods which are capable of identifying (or quantifying) the level of APF in a sample can be used for this purpose.

The level of APF present in the urine of a suspected IC patient can be detected by incubating primary normal adult human bladder epithelial cells (HBE) with whole urine from a suspected IC patient. Proliferation of HBE cells is then measured by any method known in the art including, but not limited to, determining the level of inhibition of $^3$H-thymidine or BrdU incorporation in the cells in vitro and comparing it to level of proliferation of HBE cells incubated with or without urine from age-, race- and sex-matched control persons without urologic disease.

Alternatively, APF can be assayed using an antibody, and especially a monoclonal antibody (or a fragment of either a polyclonal or a monoclonal antibody) which is capable of binding to APF.

Diagnostic assays to detect APF may comprise a biopsy or in situ assay of cells or of organ or tissue sections in addition to assays conducted upon cellular extracts from organs, tissues, cells, urine, or serum.

The antibodies (or fragments thereof) of the present invention are particularly suited for use in immunoassays wherein they may be utilized in liquid phase or bound to a solid-phase carrier.

Antibodies to APF, or fragments thereof, may be labeled using any of a variety of labels and method of labeling. Examples of types of labels which can be used in the present invention include, but are not limited to, enzyme labels, radioisotopic labels, non-radioactive isotopic labels, fluorescent labels, and cheniluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{32}$P, $^{35}$S, $^{14}$C, $^{57}$To, $^{58}$Co, $^{59}$Fe, $^{75}$Se, $^{152}$Eu, $^{90}$Y, $^{67}$Cu, $^{21}$Ci, $^{211}$At, $^{212}$Pb, $^{47}$Sc, $^{109}$Pd, etc.

Examples of suitable non-radioactive isotopic labels include $^{157}$Gd, $^{55}$Mn, $^{162}$Dy, $^{52}$Tr, $^{46}$Fe, etc.

Examples of suitable fluorescent labels include a $^{152}$Eu label, a fluorescein label, an isothiocyanate label, a rhodamine label, a phycoerythrin label, a phycodyanin label, an allophycocyanin label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label,etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1–31), and Schurs, A. H. W. M., et al. 1977 (*Clin. Chim Acta* 81:1–40). Coupling techniques mentioned in the latter are the glutaraldehyde method, the periodate method, the dimaleimide method, and others, all of which are incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to APF. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The antibodies, or fragments of antibodies of APF may be used to quantitatively or qualitatively detect the presence of activated APF. Such detection may be accomplished using any of a variety of immunoassays known to persons of ordinary skill in the art such as radioimmunoassays, immunometic assays, etc. Using standard methodology well known in the art, a diagnostic assay can be constructed by coating on a surface (i.e. a solid support) for example, a microtitration plate or a membrane (e.g. nitrocellulose membrane), antibodies specific for APF or a portion of APF, and contacting it with a patient sample such as urine from a person suspected of having IC. The presence of a resulting complex formed between APF in the urine and antibodies specific therefor can be detected by any of the known detection methods common in the art such as fluorescent antibody spectroscopy or colorimetry. A good description of a radioimmune assay may be found in *Laboratory Techniques and Biochemistry in Molecular Biology*. by Work, T. S., et al. North Holland Publishing Company, N.Y. (1978), incorporated by reference herein. Sandwich assays are described by Wide at pages 199–206 of *Radioimmune Assay Method*, edited by Kirkham and Hunter, E. & S. Livingstone, Edinburgh, 1970.

B.Therapeutic Uses

Agents which decrease the level of APF (i.e. in a human or an animal) or inhibit APF activity may be used in the therapy of any disease associated with the presence of APF. APF, or agents which increase the level of APF, or agonists of APF, may be used in the therapy of any disease associated with a decrease of APF, or an increase in cell proliferation wherein APF is capable of decreasing or inhibiting such proliferation, e.g. bladder carcinoma.

In providing a patient with antibodies, or fragments thereof, capable of binding to APF, or an agent capable of inhibiting APF, the dosage of administered agent will vary depending upon such factors as the patient's age, weight, height, sex, general medical condition, previous medical history, etc. Similarly, when providing a patient with an agent or agonist capable of inducing or increasing expression of APF, the dosage will vary depending upon such factors as the patient's age, weight, height, medical history, etc. In general, it is desirable to provide the recipient with a dosage of antibody which is in the range of from about 1 pg/kg to 10 mg/kg (body weight of patient), although a lower or higher dosage may be administered.

The compounds of the present invention may be administered to patients intravesically, intravenously, intramuscularly, subcutaneously, enterally, or parenterally. When administering such compounds by injection, the administration may be by continuous infusion, or by single or multiple boluses.

The antibodies or compounds capable of inhibiting APF, that is inhibiting either the production or activity of APF, are intended to be provided to recipient subjects in an amount sufficient to effect the inhibition of APF. Similarly, agents which are capable of inducing the expression, production, stability or function of APF, are intended to be provided to recipient subjects in an amount sufficient to effect the induction of APF. An amount is said to be sufficient to "effect" the inhibition or induction of APF if the dosage, route of administration, etc. of the agent are sufficient to influence such a response.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* [16th ed., Osol, A. ed., Mack Easton PA. (1980)]. In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacrylate)microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

A method of determining antagonists against APF is by using techniques of combinatorial chemistry and high-throughput screening (HTS). HTS is a process by which large numbers of compounds can be tested, in a automated fashion, for activity of inhibitors or activators of a particular biological target, such as APF. The primary goal is to identify high-quality 'hits' or 'leads' (compounds that affect the target in a desired manner) that are active at a fairly low concentration and that have a new structure. The lower the concentration at which the compound acts, the more likely that it will exhibit specificity and, as a corollary, the less likely that it will have undesired side effects. (Broach & Thorner *Nature* 384:14–16 (1996).

An HTS requires four elements: (1) suitably arrayed compound libraries; (2) an assay method configured for automation; (3) a robotics workstations; (4) a computerized system for handling the data. The 96-well microtiter plate is the standard format for automated assays, although arrays of compounds on chips or on beads are also used and assays can be performed on agar plates or other solid support. Synthesis of combinatorial libraries can be accomplished in microtiter plates, thereby providing addresses for particular compounds generated by a given subset or series of reactions and thus identifying the compound. For further information on how to use HTS for determining antagonist/agonist compounds for APF, see (Broach & Thorner *Nature* 384:14–16 (1996).

Having now generally described the invention, the same will be more readily understood through reference to the following examples which are provided by way of illustration, and are not intended to be limiting to the present invention, unless specified.

The following Materials and Methods were used in the Examples described below.

Patients

IC patients were referred by physicians, the National Institute of Diabetes and Digestive and Kidney Diseases (NIDDK), and the Interstitial Cystitis Association. All patients had previously undergone diagnostic cystoscopy, and fulfilled the NIDDK diagnostic criteria for IC [Division of Kidney, Urologic, and Hematologic Diseases (DKUHK) of the National Institute of Diabetes and Digestive and Kidney Diseases (NIDDK)(1989) *Am J. Kidney Dis.* 13:353]; urine was collected from these patients at least three months following the most recent known bacterial urinary tract infection and one month following the last antibiotic use. Age-, race- and sex-matched controls were volunteers with no history of IC or other urological disease, or patients undergoing cystoscopy for other urological disease (including benign stricture of the ureteropelvic junction, glomerulosclerosis of the kidney, caliceal diverticulum with stones, ureteral endometriosis, and renal cell carcinoma); each control patient was required to have no symptoms of urinary tract infection or antibiotic use for at least one month. All participants were at least 18 years old and enrolled in accordance with guidelines of the Institutional Review Board at the University of Maryland School of Medicine. The number of IC patients or controls used for each experiment was based on the number for whom a sufficient quantity of urine was available for each experiment. However, each IC patient urine specimen was studied simultaneously with urine from one or two age-, race- and sex-matched controls for each experiment.

In later experiments, IC patients were referred by physicians and the Interstitial Cystitis Association. All patients had previously undergone diagnostic cystoscopy, and fulfilled the NIDDK diagnostic criteria for IC. Asymptomatic controls were age-, race-, and sex-matched volunteers with no history of IC or other urological disease. Patients with acute bacterial cystitis were identified by the presence of bacteriuria (>$10^3$ bacteria/ml of a single type of bacterium; 17/20 patients had >$10^5$ bacteria/ml) plus pyuria in combination with appropriate symptoms. Vulvovaginitis was diagnosed by physical examination. All participants were at least 18 years old and enrolled in accordance with guidelines of the Institutional Review Boards at the University of Maryland School of Medicine and the University of Pennsylvania at Philadelphia.

Urine Specimens

Urine was collected either by catheterization, as previously described [Keay et al. (1995) *Urology* 45: 223], or by the clean catch method in which each patient wiped the labial area with 10% povidone iodine/titratable iodine 1% solution (Clinidine, Guilford, Conn.), then collected a midstream urine into a sterile container). Specimens were initially kept at 4° C., transported to the laboratory within one hour of collection, aliquoted under sterile conditions, and plated directly onto confluent cells for cytotoxicity assays or stored at −80° C. until used.

In later experiments, urine was collected by the clean catch method as described above. Specimens were initially frozen at 20° C., transported to the laboratory on ice, thawed, aliquoted under sterile conditions, and stored at −80° C. until used.

Cell Culture

T24 bladder carcinoma cells (ATCC #4-HTB) (Rockville, Md.) were grown in McCoy's medium containing 10% fetal bovine serum (FBS), 1% antibiotic/antimycotic solution, and 1% glutamine (Sigma, St. Louis, Mo.).

Normal adult human bladder epithelial cells (HBE) were grown from biopsies obtained at autopsy from patients who had no history of bladder disorder [Trifillis,et al. (1993) *In vitrol Cell Dev. Biol.* 29A:908]. The explanted cells were grown in Eagle's minimal essential medium (MEM) containing 10% heat inactivated FBS, 1% antibiotic/antimycotic solution, 1% glutamine, and 1.0 ug/ml insulin (all from Sigma).

Normal human fetal bladder cells FHS 738 B1 (ATCC #160-HTB) were grown in DMEM containing 1000 mg/L glucose, 10% fetal bovine serum, 1% antibiotic/antimycotic solution, 1% glutamine, and 3.5 ug/ml insulin (all from Sigma). All cells were cultured at 37° C. in a 5% $CO_2$ atmosphere.

$^3$H-Thymidine Incorporation

HBE cells explanted from bladder tissue or FHS 738 B1 cells were plated at a density of $1\times10^4$ cells/well onto 96 well tissue culture plates and incubated at 37° C. overnight (resulting in approximately 60% confluence the following day). The medium was then changed to MEM containing only 1% glutamine and 1% antibiotic/antimycotic solution, and the cells were incubated at 37° C. overnight. On the third day urine specimens from IC patients and control were corrected to pH 7.2 and 300 mOsm, filtered, diluted in MEM (with only glutamine and antibiotics/antimycotics) and applied to the cells. (Undiluted IC patient or control urine was uniformly extremely toxic in initial experiments, indicating the need for cell culture medium to support the growth of these cells in vitro). Following 48 hours of incubation at 37° C., the cells were pulsed with 1.0 uCi $^3$H-thymidine/well (NEN DuPont, Wilmington, Del.) and incubated for another 4 hours at 37° C. Cells were trypsinized, lysed with deionized/distilled water, and insoluble cell contents harvested and methanol-fixed onto glass fiber filter paper using a PHD cell harvester (Cambridge Technology, Inc., Watertown, Mass.); the amount of radioactivity incorporated was determined as counts per minute using a Beckman LS 3801 scintillation counter.

Bromodeoxyuridine (BrdU) Incorporation:

HBE cells were cultured in 96 well plates and urine specimens applied as described above for the $^3$H-thymidine incorporation assay. Following 48 hours of incubation with the urine specimens, the cell medium was removed and cells were incubated with BrdU labeling solution (Boehringer-Mannhiem) for 4 hours at 37° C., according to the manufacturer's directions. This solution was then removed, FIXDENAT solution applied, and the cells incubated at room temperature for 30 minutes. The cells were then further incubated with anti-BrdU-peroxidase-labeled antibody, rinsed 3 times with a washing solution, and developed with a substrate solution. Development was stopped with 1M H2SO4 and absorbance read at 450 nm.

Dialysis of Urine Specimens

Urine specimens were dialyzed against PBS at 4° C. overnight, using Spectra/Por Membranes (Spectrum Medical Industries, Houston, Tex.) with pore sizes that allowed removal of substances less than 1,000, less than 10,000 or less than 25,000 daltons. The specimens were then removed and pH adjusted to 7.2, as above. The volume recovered for each specimen following dialysis was 90–100% of the original starting volume.

Trypsinization of Urine

Urine was incubated with 8.25 U/ml trypsin conjugated to agarose beads in Hank's buffer (Sigma) at 37° C. for 2 hours, after which the beads were removed by centrifugation, pH and osmolality of the urine adjusted, and $^3$H-thymidine incorporation assay performed. Duplicate control specimens were incubated with an equivalent amount of Hank's buffer at 37° C. for 2 hours.

Statistical Analysis

Differences in the number of specimens causing significant inhibition of $^3$H-thymidine or BrdU incorporation were analyzed by Fisher's exact test (where significant inhibition was defined as a decrease greater than 2 standard deviations from the mean of controls). Comparisons of mean change in $^3$H-thymidine incorporation caused by undialyzed vs. dialyzed urine specimens were performed using a one-way analysis of variance with Scheffe's test for multiple comparisons (IC patient and control specimens analyzed separately).

In later experiments, comparison of the number of IC patients and controls whose urine inhibited cell proliferation was performed using Fisher's exact test; significant inhibition was defined as a decrease in 3H-thymidine or BrdU incorporation greater than 2 standard deviations from the mean of untreated control cells. A comparison of the mean percent change in 3H-thymidine incorporation for the IC group vs. each of the 3 control groups was also made using a two tailed analysis of covariance with age as the covariate.

EXAMPLE 1

Figure 1A:
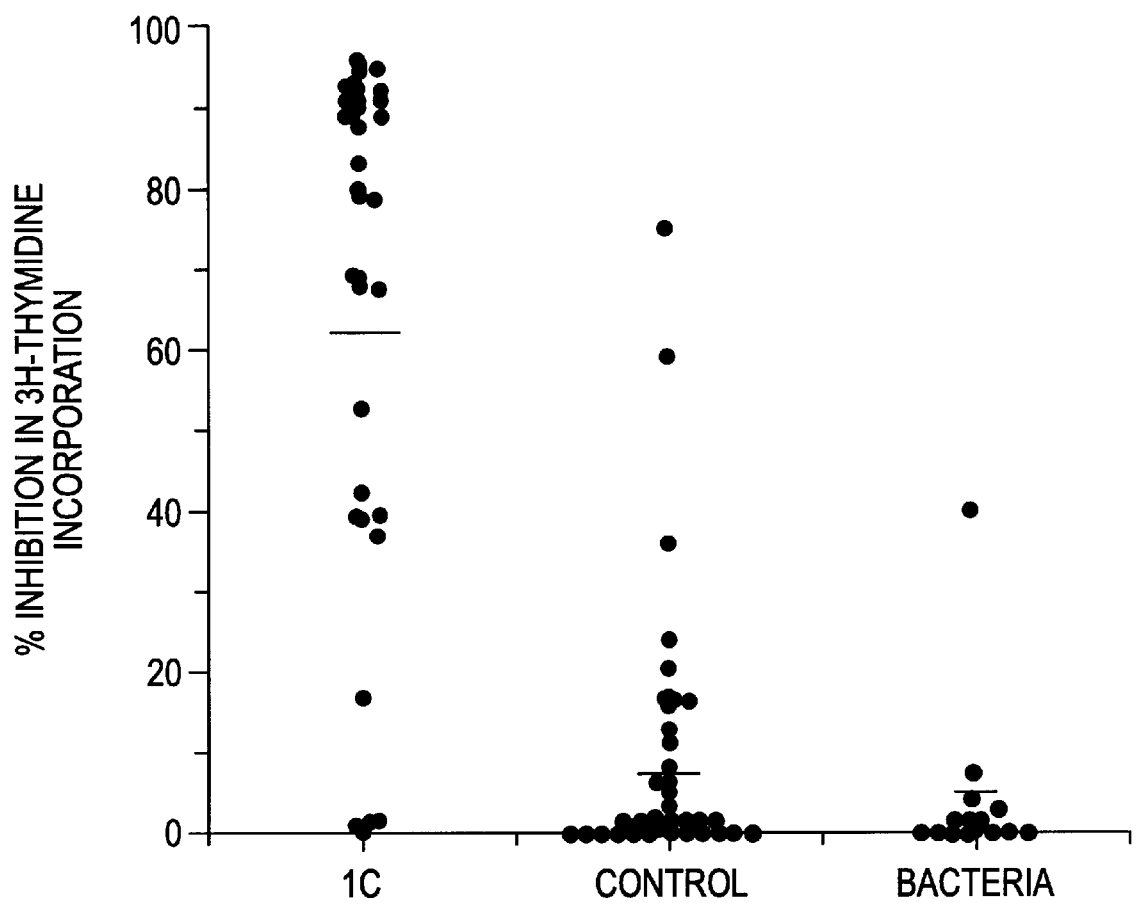
FIG. 1A: Inhibition of cell proliferation by IC patient urine specimens, asymptomatic controls, and bacterial cystitis patients ($^3$H-thymidine incorporation).
Figure 1B:
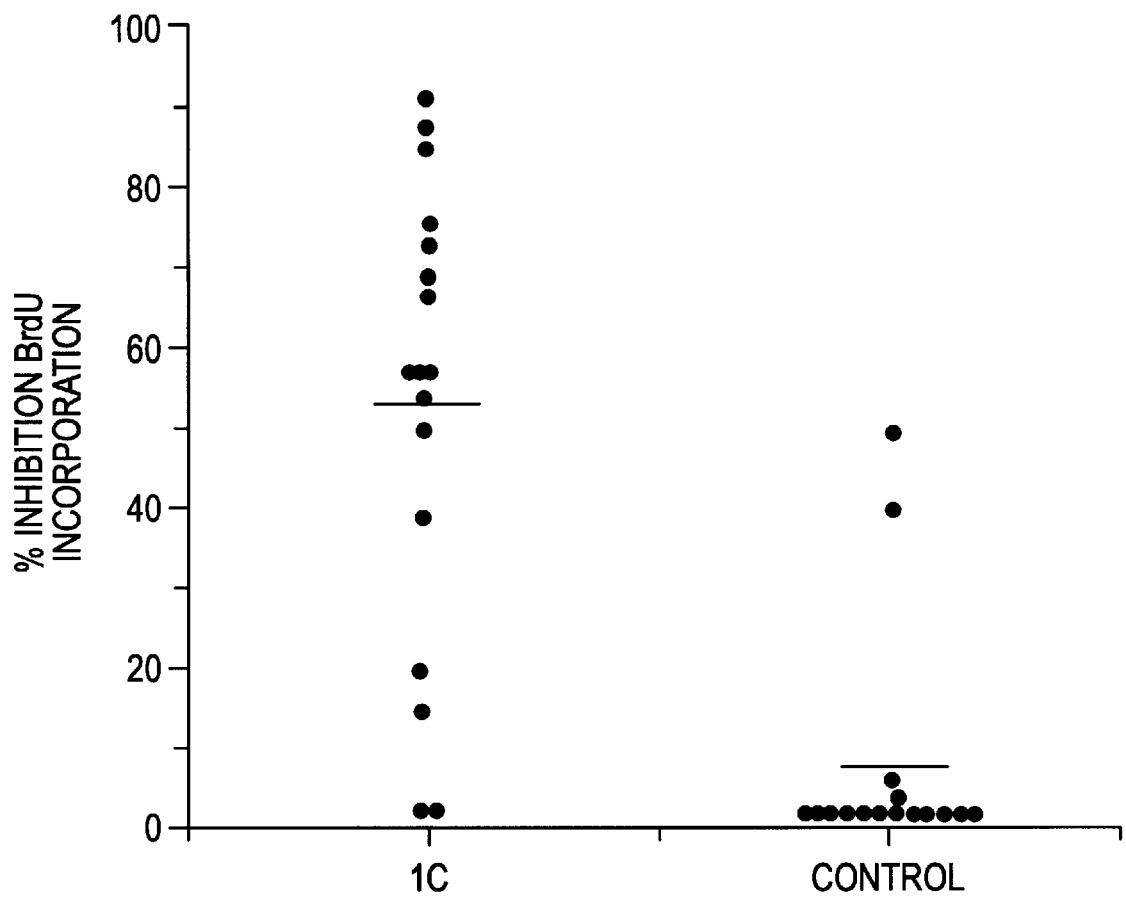
FIG. 1B: Inhibition of BrdU incorporation in normal adult human bladder epithelial cells by IC patient urine specimens and asymptomatic controls.

Identification of a Putative Antiproliferative Factor (APF) in Urine from IC Patients IC patients whose diagnosis was confirmed by cystoscopy at the University of Maryland and who fulfilled criteria established by the NIDDK were studied. Primary normal adult human bladder epithelial (HBE) cells were incubated with whole urine specimens from these IC patients or age-, race- and sex-matched controls. Prior to their addition to the cell culture medium, all specimens were corrected for osmolality (300 mOsm) and pH (7.0). Our data indicate that the proliferation of HBE cells is inhibited by urine from IC patients as compared to age-, race- and sex-matched controls without urologic disease and to patients with bacterial cystitis. Specimens from 22 of 29 (76%) IC patients vs. 2 of 33 (6%) controls inhibited HBE cell proliferation significantly as determined by $^3$H thymidine incorporation in vitro (FIG. 1A; p <0.001, Fisher's exact test analysis; significant inhibition was defined as a decrease greater than 2 standard deviations from the mean of untreated control cells). This finding was confirmed by bromodeoxyuridine incorporation using specimens from a subset of these patients [12 of 16, or 75% of IC patients had significant inhibition vs. 2 of 16, or 12% of controls (FIG. 1B; p=0.001 by Fischer's exact test)].

Figure 1C:
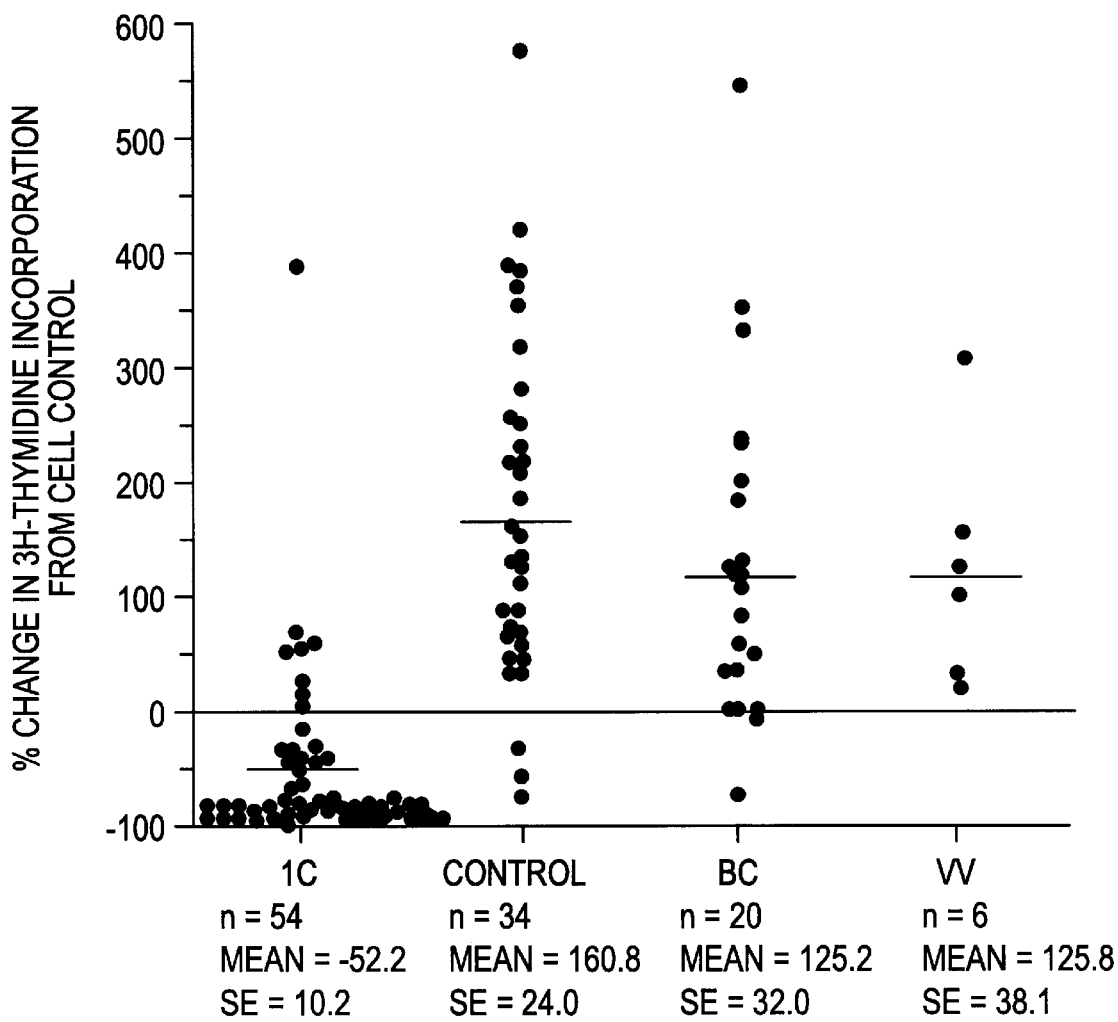
FIG. 1C: Inhibition of cell proliferation by IC patient urine specimens, asymptomatic controls, patients with bacterial cystitis (BC), or patients with vulvovaginitis (VV) ($^3$H-thymidine incorporation).
Figure 1E:
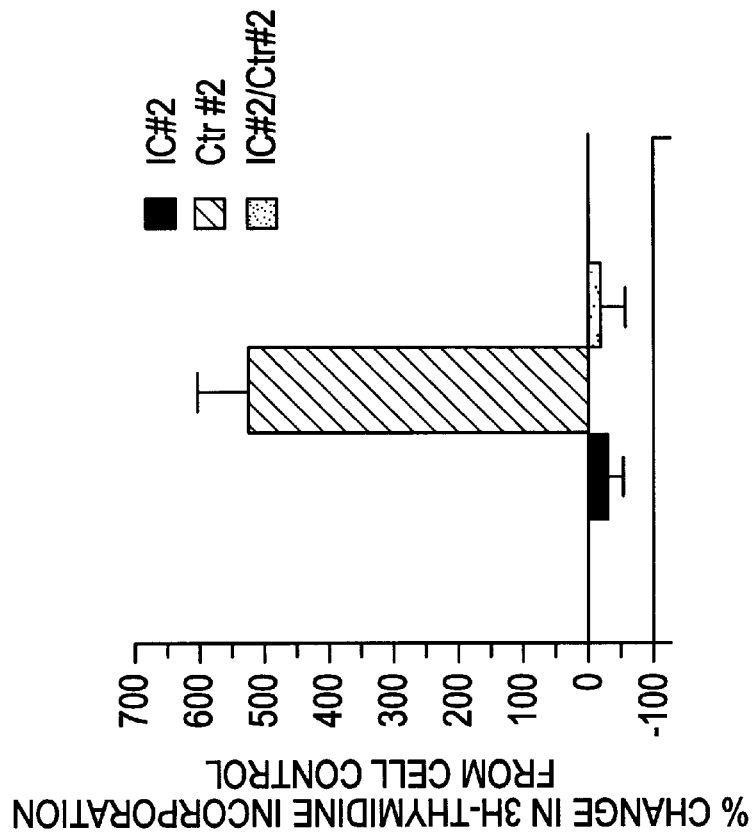
FIG. 1E: Net inhibition of HBE cell proliferation by IC patient #2 and control urine specimens.

To determine the reproducibility and specificity of this finding, we have expanded on the initial studies and to date have screened urine from 54 women with IC (mean age 44.1+/-2.0 years), 34 asymptomatic control women (mean age 41.0+/-2.0 years), 20 women with documented bacterial cystitis (mean age 24.3+/-1.4 years) and 6 women with vulvovaginitis (mean age 37.0+/-5.6 year) for antiproliferative urine activity by $^3$H-thymidine incorporation. Specimens from 46 of 54 (85%) IC patients inhibited human bladder epithelial cell proliferation in vitro, as compared to 3 of 34 (9%) asymptomatic controls, 2 of 20 (10%) patients with bacterial cystitis, and 0 of 6 (0%) women with vulvovaginitis. The mean percent change in $^3$H thymidine incorporation in cells cultured with IC urine was -52.2+/-10.2, as compared to +160.8+/-24.0 for asymptomatic controls, +125.2+/-32.0 for bacterial cystitis patients and +125.8+/-38.1 for vulvovaginitis patients (FIG. 1C, p<0.001 for each comparison of the IC group to each of the 3 control groups using a two tailed analysis of covariance with age as the covariate.) Each data point is the mean of six samples. Mean value and standard error for the population are indicated for each group.

Demonstration of Potential Diagnostic Utility of APF

The potential diagnostic utility of the APF was demonstrated by determining the sensitivity, specificity, positive predictive value and negative predictive value of a significant decrease in $^3$H-thymidine or BrdU incorporation (defined as a decrease greater than 2 standard deviations from the mean of untreated control cells). Data from the 29 IC patients and 33 controls indicated a sensitivity of 76% and specificity of 94% for $^3$H-thymidine incorporation, and data from 16 IC patients and 16 controls indicated a sensitivity of 75% and a specificity of 88% for BrdU incorporation (Table 1). The positive predictive value and negative predictive value were 92% and 82% for $^3$H-thymidine incorporation and 86% and 78% for BrdU incorporation, respectively.

Data from the the expanded studies using 54 IC patients and 34 asymptomatic controls indicated a sensitivity of 85% and a specificity of 91% for $^3$H-thymidine incorporation. The positive predictive value and negative predictive value were 94% and 80% for $^3$H-thymidine incorporation.

TABLE 1

Inhibition of Bladder Cell Proliferation as a Diagnostic Assay for IC

|  | $^3$H-Thymidine Incorporation Initial Studies/Expanded Studies | BrdU Incorporation |
| --- | --- | --- |
| Sensitivity | 76%/85% | 75% |
| Specificity | 94%/91% | 88% |
| Positive Predictive Value | 92%/94% | 86% |
| Negative Predictive Value | 82%/80% | 78% |

Figure 1D:
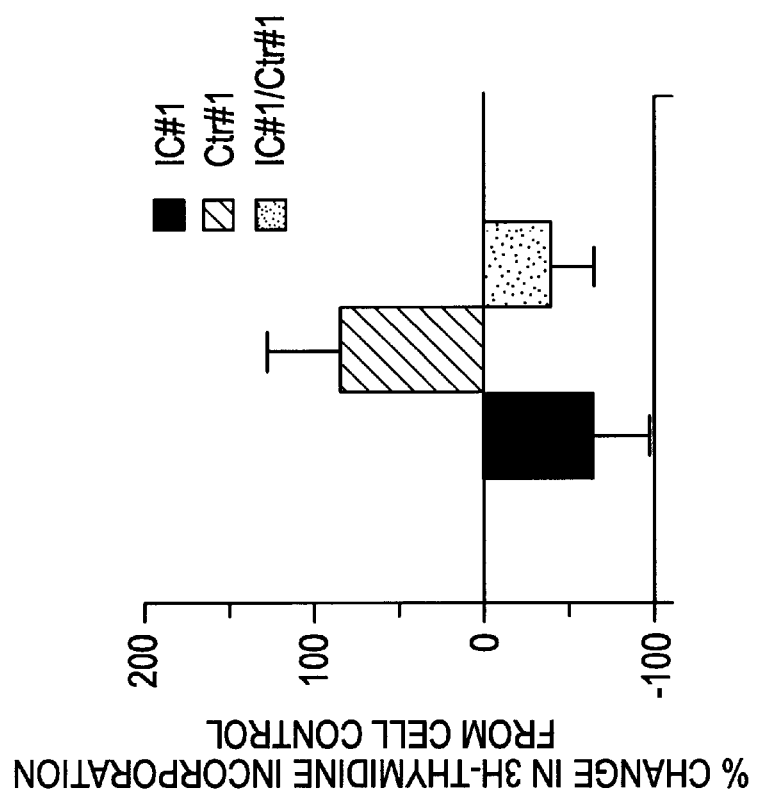
FIG. 1D: Net inhibition of HBE cell proliferation by IC patient #1 and control urine specimens.

Demonstration of the antiproliferative effect required prior serum starvation of the HBE cells and more than 24 hours of exposure to IC urine. These requirements suggested an effect on the process of cell proliferation rather than a directly toxic effect. The lack of a difference in trypan blue exclusion between cells exposed to IC or control urine, or evidence for apoptotic DNA breakdown in cells exposed to IC urine, supported this hypothesis (data not shown). The effect of serial dilution of urine on $^3$H thymidine incorporation was then examined, to determine whether the decreased incorporation in response to IC urine resulted from lack of a urine growth factor(s) or presence of an inhibitory factor(s). The greatest inhibition of $^3$H-thymidine incorporation occurred in response to the highest concentration of urine from IC patients; serial dilution of the inhibitory effect suggested the presence of an antiproliferative factor (APF) in IC urine. Additional evidence that the urine of IC patients contains a factor that actively inhibits bladder epithelial cell proliferation was provided by recent experiments that demonstrated net inhibition of $^3$H-thymidine incorporation in response to the addition of equal volumes of IC urine and control urine to the cell medium. More specifically, HBE cells were cultured in the presence of 1) the less than 10 kD fractionation of urine from either of 2 IC patients, 2) the less than 10 kD fraction of urine from their age-, race-, and sex-matched controls, 3) a combination of equal parts of less than 10 kD fractions of IC and control urine, or 4) serum-free cell culture medium alone, for 48 hours prior to performance of the cell proliferation assay. Specimens were diluted in serum-free medium such that the final concentration of either IC or control urine was the same in each well that contained a particular specimen. Data are expressed as the mean percent change in $^3$H-thymidine incorporation for cells cultured with urine specimens as compared to cells cultured in serum-free culture medium alone (FIG. 1D).

EXAMPLE 2

Inhibition of T24 carcinoma cell proliferation by IC patient urine specimens

T24 bladder carcinoma cells (ATCC #4-HTB) (Rockville, Md.) were grown in McCoy's medium containing 10% fetal bovine serum (FBS), 1% antibiotic/antimycotic solution, and 1% glutamine (Sigma, St. Louis, Mo.). These cells were seeded onto 96 well tissue culture plates (Corning Glass Works, Corning, N.Y.) at a density of $5 \times 10^3$ cells/well, and incubated overnight. The pH of IC patient or control urine specimens was adjusted to 7.0 by the addition of 10 N NaOH or 1 N HCl, and the osmolality was adjusted to 300 mOsm by the addition of 1 M NaCl or distilled $H_2O$. Varying dilutions of urine specimens in standard culture medium were added to the cells, which were then incubated further at 37° C. for 48 hours prior to performance of the $^3H$ thymidine incorporation assay.

Figure 2:
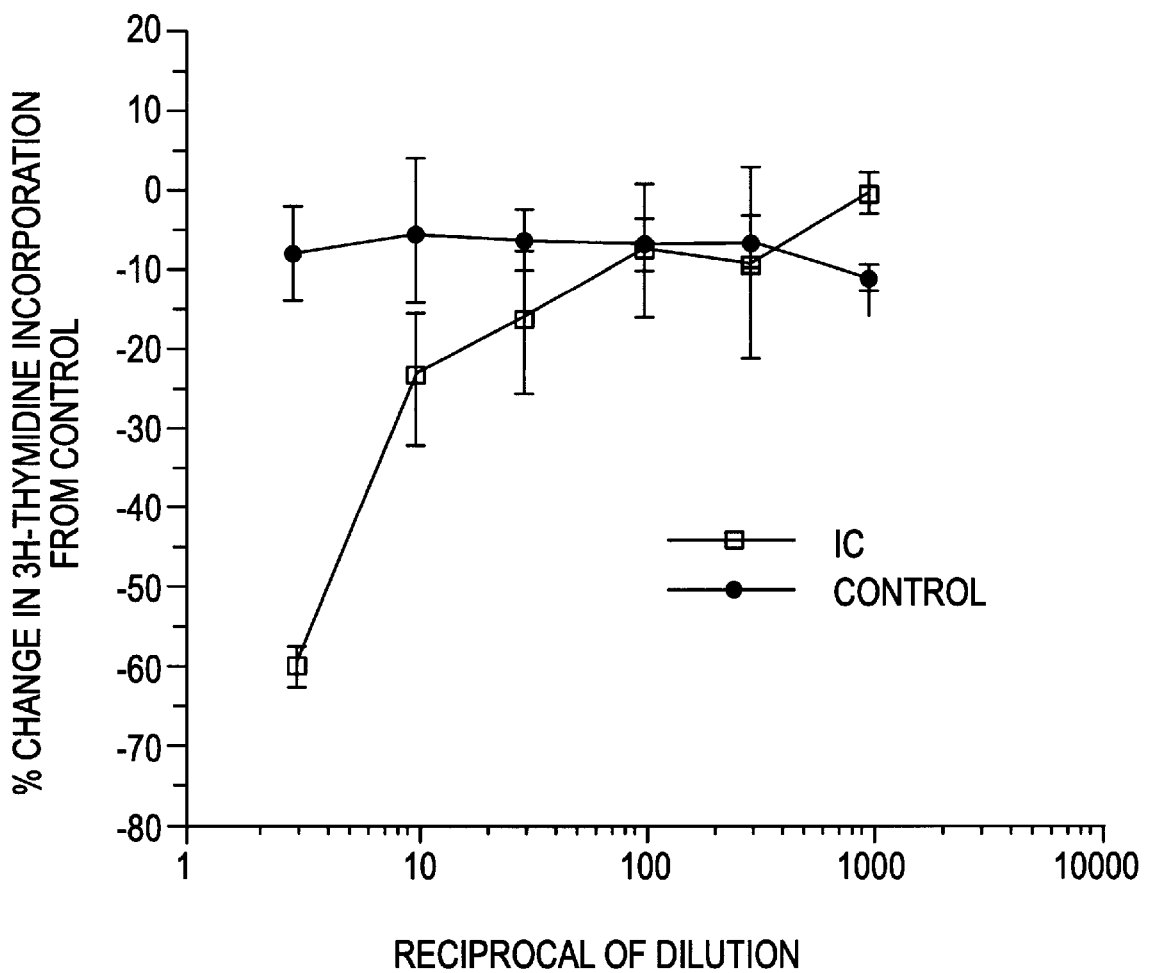
FIG. 2: Inhibition of T24 carcinoma cell proliferation by IC patient urine specimens.

Although control urine specimens did not stimulate the proliferation of T24 cells (which were derived from a malignant human tumor and do not have a finite life span in vitro) IC urine specimens inhibited their proliferation (FIG. 2). These data suggest that this APF may be able to inhibit the proliferation of both normal and immortalized cells, suggesting its potential use to control tumor cell proliferation.

EXAMPLE 3

Characterization of APF

Studies to determine the stability of the APF in IC urine indicated this factor was fairly stable to a freeze-thaw cycle, with only 18.5±8.2% loss of activity. Heating of the IC urine specimens resulted in unchanged antiproliferative activity (% change in $^3H$-thymidine incorporation of cells incubated with IC urine compared to cells incubated with medium alone=−62.0±6.8 for unheated specimens, to −60.7±14.0 for specimens heated to −70° C. for 2 hours).

To determine whether the APF was protein in nature, its susceptibility to proteases was also examined. Trypsinization of seven IC urine specimens effectively removed most of the antiproliferative activity (D=loss of 87.5±26.7% of antiproliferative activity compared to untrypsinized control exposed to the same incubation conditions).

Figure 3:
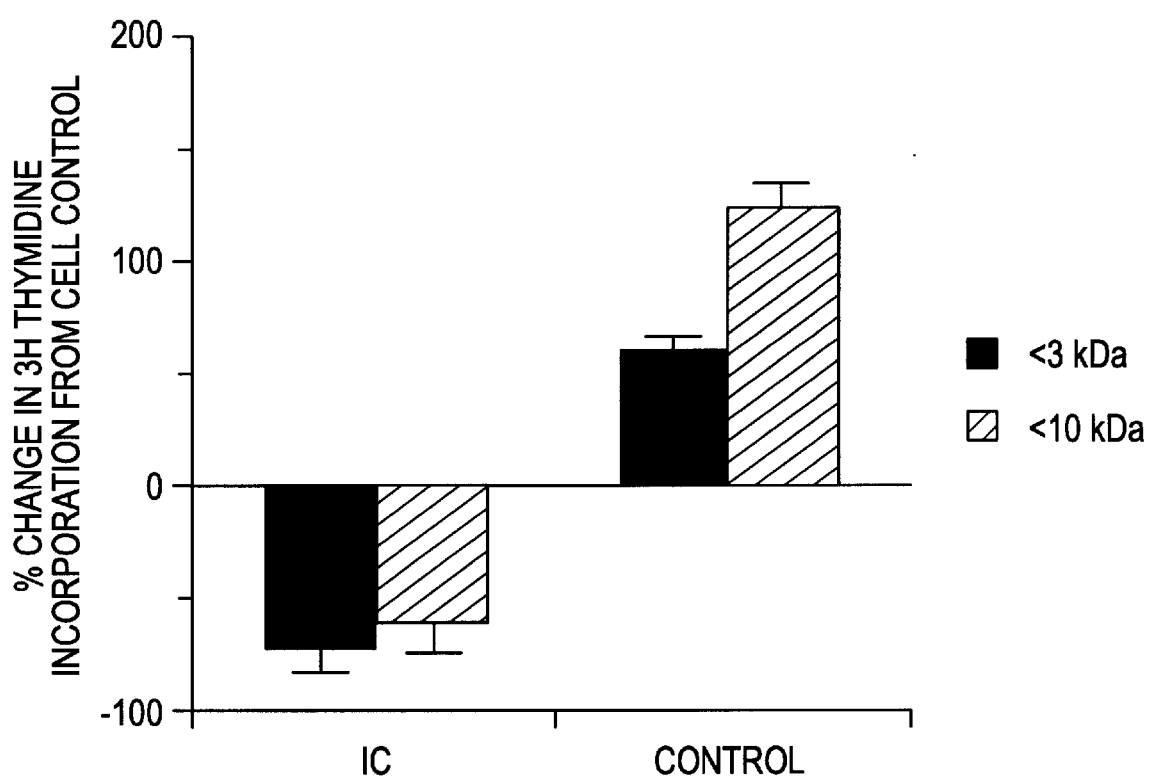
FIG. 3: Inhibition of human bladder cell proliferation by low molecular weight fractions from IC urine.

The approximate size of the putative antiproliferative protein was initially determined by dialysis. Dialysis of substances less than 10,000 daltons resulted in effective removal of the APF, while dialysis of substances less than 1000 daltons retained the factor. These findings were confirmed by fractionation of the inhibitory IC specimens using "CENTRIPREP" filters; IC urine fractions of substances <10 kDa inhibited bladder epithelial cell proliferation to the same degree as whole urine, while the same fractions from controls were stimulatory. These data suggest that the antiproliferative effect of IC patient urine is due to the presence of a 1–10 kDa relatively heat stable protein(s). Recent experiments using the fraction filtered through a 3000 dalton cut-off "CENTRIPREP" filter have indicated that the molecular weight range for the APF is actually 1–3 kDa (FIG. 3).

EXAMPLE 4

Separation of low molecular weight urinary components by ion-exchange chromatography The <10,000 dalton fraction of 500 ml of urine from an IC patient was loaded onto a "MONO Q" sepharose preparative column and components eluted with 1 M NaCl. Each fraction was then tested for its ability to inhibit $^3H$-thymidine incorporation into normal human bladder cells. Data in FIG. 5 are expressed as the mean % inhibition of $^3H$-thymidine incorporation in cells incubated with IC patient urine specimens compared to cells incubated with serum-free cell culture medium alone. Each data point is the mean of three samples; bars indicate standard error of the mean. The line indicates the osmolarity generated by the NaCl gradient.

Using this method of peptide purification we were able to elute several fractions (contained within one broad peak) having anti-proliferative activity. We therefore used ion-exchange chromatography as a preliminary purification step for APF.

EXAMPLE 5

Separation of low molecular weight urinary components using hydrophobic interaction chromatography The <10,000 dalton fraction of urine from an IC patient was loaded onto a phenyl sepharose 6 fast flow (high sub) column in 1 M ammonium sulfate buffer, and components were eluted using 50 mM sodium phosphate buffer (pH 7.0). Each fraction was then tested for its ability to inhibit $^3H$-thymidine incorporation into normal human bladder cells. Data in FIG. 6 are expressed as % change in cpm of cells incubated with IC patient urine specimens compared to cells incubated with serum-free cell culture medium alone. Each data point is the mean of three samples; bars indicate standard error of the mean.

Using this purification method, we were able to obtain a single fraction with significant inhibitory activity. We therefore used this method of hydrophobic interaction chromatography subsequent to ion-exchange chromatography for further purification of the APF.

EXAMPLE 6

Identification of a Single Peak Representing APF by High Performance Liquid Chromatography Preliminary attempts to purify APF from the <10 kD urine fraction of five IC patients by HPLC indicated the presence of a single peak fraction that inhibited $^3H$ thymidine incorporation into HBE cells (data shown for one patient, FIG. 4). No inhibitory fraction was identified in the <10 kD fraction from five age-, race-, and sex-matched controls (data not shown).

Figure 7A:
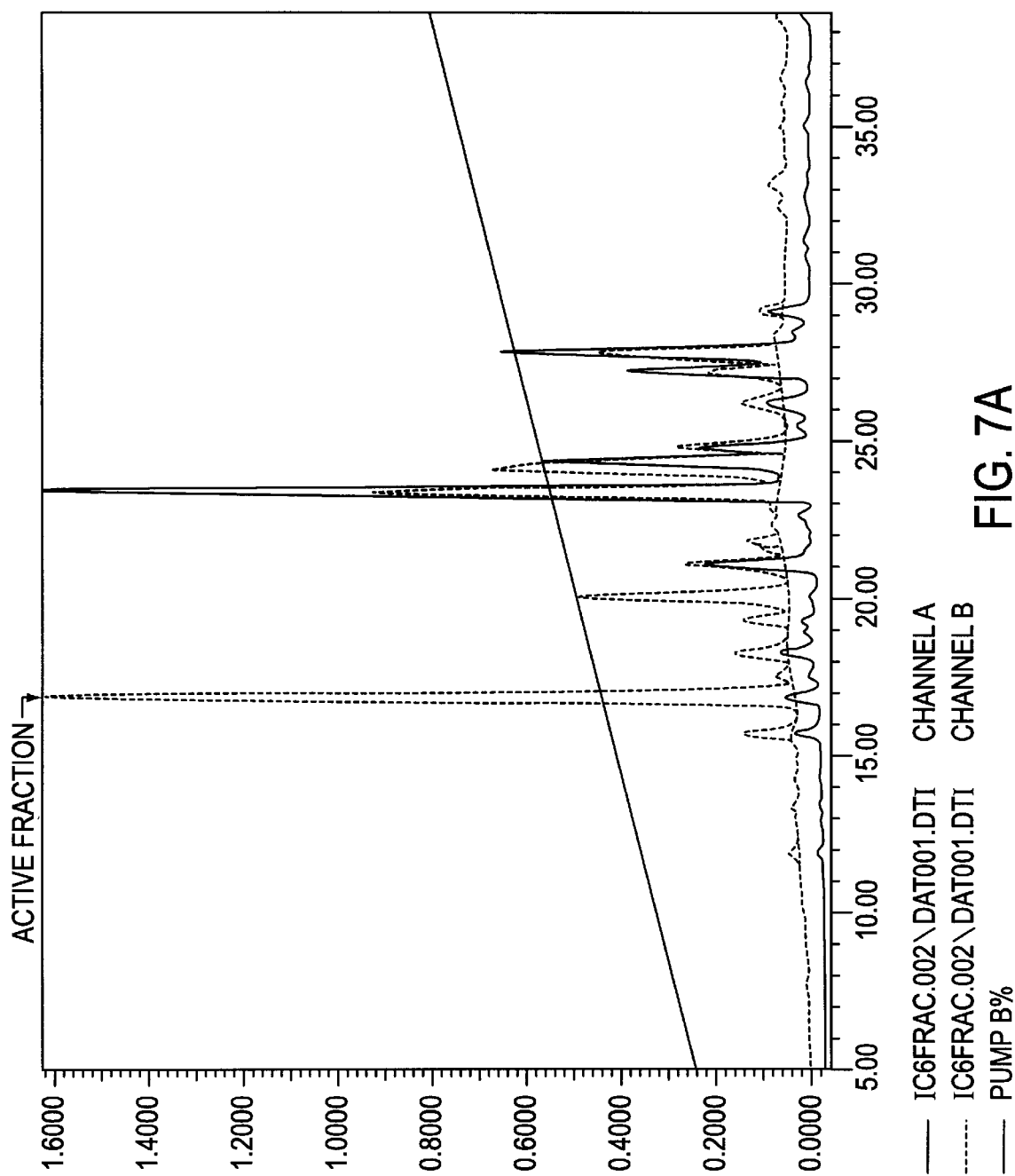
FIG. 7A: Separation of low molecular weight urinary components by HPLC.

Therefore following ion-exchange chromatography and hydrophobic interaction chromatography, we used HPLC as a final step in the purification scheme of APF. This scheme yielded several peaks at absorbance 215/280 nm. Indicated is the HPLC acetonitrile elution profiles (215/280 nm absorbance) of IC patient urine with active antiproliferative fraction indicated by arrow in FIG. 7A. The single fraction with antiproliferative activity was reapplied to the HPLC column, and the elution profile which indicates purification to homogeneity is indicated by FIG. 7B.

The same purification scheme, employing ion-exchange chromatography, hydrophobic interaction chromatography, and HPLC, has been applied to the less than 10 kDa fraction of urine from control patients. Mock APF fractions from the HPLC acetonitrile elution of control patient specimens failed to show any antiproliferative activity by the inhibition of 3H-thymidine incorporation assay.

EXAMPLE 7

Characterization by Mass Spectrometry and Amino Acid Analysis

Figure 8:
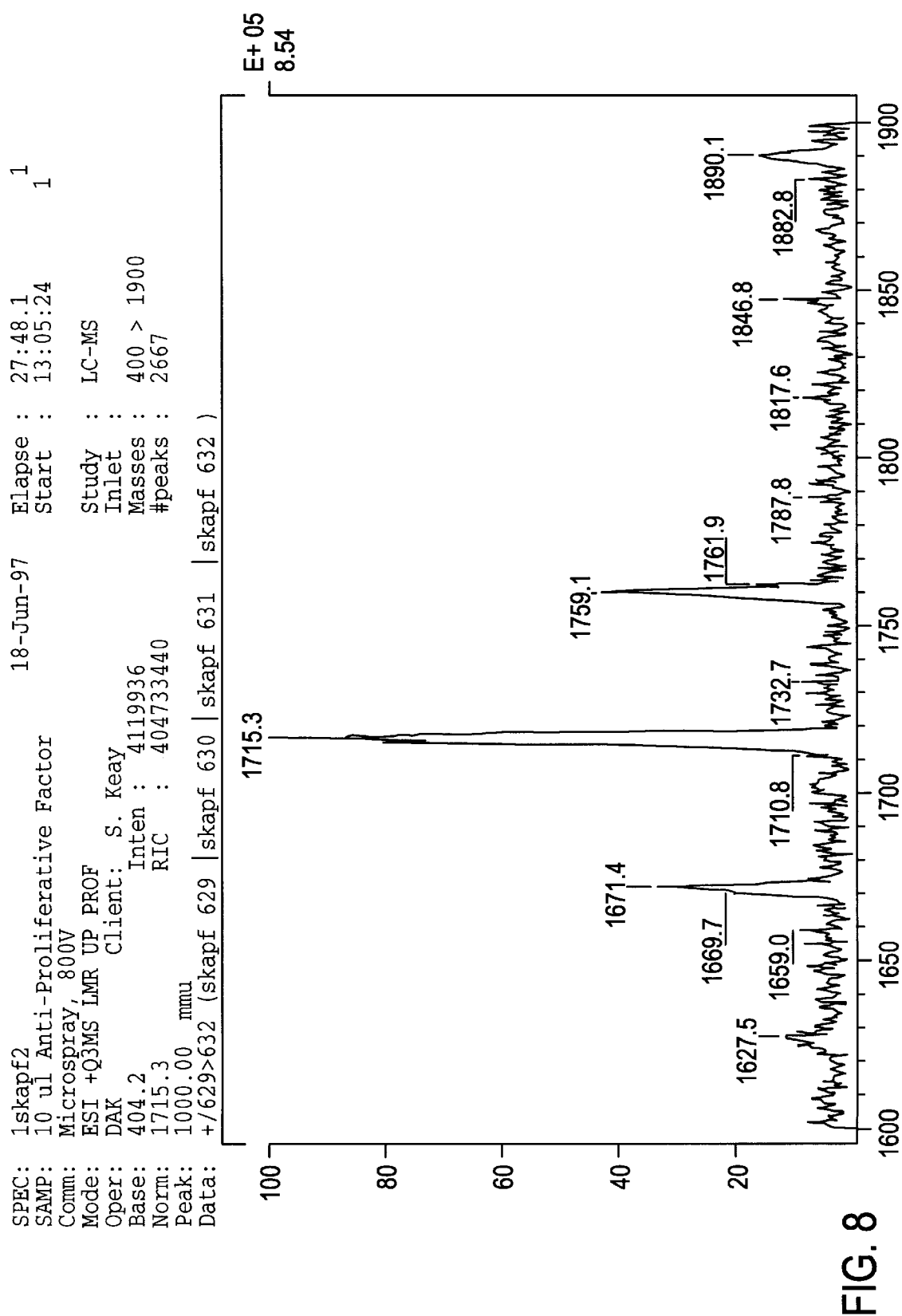
FIG. 8: Mass spectrometric analysis of APF molecular mass.

A 10 ul sample of APF was analyzed by quadripole mass spectrometry and produced the profile seen in FIG. 8. As seen in FIG. 8, APF has a mass of 1671 (the two additional peaks with +44 and +88 molecular mass probably represent the peptide plus a small contaminating molecule from the sepharose column rather than an associated cation or anion, since their masses are 1671+multiples of 44).

Preliminary amino acid analysis was accomplished by ion trap mass spectrometry, and indicated a high glycine content. FIG. 9 shows the amino acid analysis of the APF peptide.

We claim:

1. Purified human antiproliferative factor (APF), said factor being isolated from the urine of patients with interstitial cystitis wherein said factor is characterized by a molecular weight of about 1.7 kDa determined by mass spectrometry on a sample in an aqueous acetonitrile solution and a pI range of about 1.38–3.5, said factor capable of inhibiting normal bladder epithelial (HBE) and bladder carcinoma cell proliferation.

2. A composition for inhibiting the activity of the APF of claim 1 comprising an antibody having binding affinity for said APF in an amount effective for inhibiting the activity of said APF in cells.

3. The composition of claim 2 wherein said cells are selected from the group consisting of tumor cells and cancer cells.

4. A functional derivative of the factor of claim 1 still capable of influencing cell proliferation, wherein said derivative is a fragment or chemical derivative of said factor.

* * * * *